US012670809B2

(12) United States Patent (10) Patent No.: US 12,670,809 B2
Cline et al. (45) Date of Patent: Jun. 30, 2026

(54) PATIENT TRAINING DEVICE FOR USE WITH A SAFETY SYRINGE INJECTOR

(71) Applicant: Merck Sharp & Dohme LLC, Rahway, NJ (US)

(72) Inventors: John B. Cline, Monroe, NJ (US); Cassie Megna, New Milford, NJ (US); Wail Rasheed, Union, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 975 days.

(21) Appl. No.: 17/798,762

(22) PCT Filed: Feb. 9, 2021

(86) PCT No.: PCT/US2021/017159
§ 371 (c)(1),
(2) Date: Aug. 10, 2022

(87) PCT Pub. No.: WO2021/163004
PCT Pub. Date: Aug. 19, 2021

(65) Prior Publication Data
US 2023/0086278 A1 Mar. 23, 2023

Related U.S. Application Data

(60) Provisional application No. 62/976,621, filed on Feb. 14, 2020.

(51) Int. Cl.
*G09B 23/28* (2006.01)
*A61M 5/32* (2006.01)

(52) U.S. Cl.
CPC ......... *G09B 23/285* (2013.01); *A61M 5/3275* (2013.01)

(58) Field of Classification Search
None
See application file for complete search history.

(56) References Cited

U.S. PATENT DOCUMENTS

| | | | |
|---|---|---|---|
| 5,411,487 A | 5/1995 | Castagna |
| 2001/0053886 A1 | 12/2001 | Caizza |
| 2013/0085455 A1 | 4/2013 | Manke et al. |
| 2014/0066862 A1 | 3/2014 | Schweers et al. |
| 2020/0043372 A1 | 2/2020 | Basile et al. |

FOREIGN PATENT DOCUMENTS

| | | |
|---|---|---|
| EP | 3181168 A1 | 6/2017 |
| WO | 2018075335 A1 | 4/2018 |

*Primary Examiner* — James B Hull
(74) *Attorney, Agent, or Firm* — Janet E. Fair; John C. Todaro

(57) ABSTRACT

The present invention provides reusable safety syringe devices for use as a teaching and practice tool. The safety syringe device of the present invention comprises four primary parts: (1) a first tubular member; (2) a second tubular member disposed within an inner annular cavity of the first tubular member; (3) a syringe secured within an inner annular cavity of the second tubular member; and (4) a plunger rod, wherein the plunger rod comprises a proximal end and a distal end, wherein the proximal end and distal end are connected by a shaft, wherein the proximal end comprises a first plunger rod flange having a first diameter and a removable second plunger rod flange having a second diameter, wherein the first diameter is smaller than the second diameter and the first plunger rod flange is located below the second plunger rod flange on the shaft.

9 Claims, 16 Drawing Sheets

PATIENT TRAINING DEVICE FOR USE WITH A SAFETY SYRINGE INJECTOR

CROSS-REFERENCE TO RELATED APPLICATIONS

This application is a U.S. National Phase application under 35 U.S.C. § 371 of PCT Application No. PCT/US2021/017159, filed Feb. 9, 2021, which published as WO 2021/163004 on Aug. 19, 2021, and claims priority under 35 U.S.C. § 365(b) from U.S. Provisional Patent Application No. 62/976,621, filed Feb. 14, 2020.

BACKGROUND OF THE INVENTION

A wide variety of drugs are administered in prefilled syringes. To limit the potential for disease transmission and needle injuries, the majority of prefilled syringes are packaged within safety devices. These devices deploy following an injection and physically cover the needle, consequently preventing needle sticks and disease transmission due to such sticks. However, once the safety device is deployed, it is locked in place to prevent reuse.

To deliver needle stick protection, the patient or caregiver must use the safety device correctly; some level of training is required to obtain proficiency of use. Typically the drug contained within the syringe is expensive and therefore too costly to be used in a training environment. Placebo syringes are far cheaper, but still expensive; and they cannot be reused.

There is a need for a low cost, reusable safety syringe trainer that can be used as a teaching tool for the caregiver and a practice tool for the patient.

SUMMARY OF THE INVENTION

The present invention provides reusable safety syringe devices for use as a teaching and practice tool using an alternative plunger design to the plunger and safety syringe described in PCT Patent Application No. WO 2018/075335. The safety syringe device of the present invention comprises of four primary parts: (1) a first tubular member; (2) a second tubular member disposed within an inner annular cavity of the first tubular member; (3) a syringe secured within an inner annular cavity of the second tubular member; and (4) a plunger rod, wherein the plunger rod comprises a proximal end and a distal end, wherein the proximal end and distal end are connected by a shaft, wherein the proximal end comprises a first plunger rod flange having a first diameter and a removable second plunger rod flange having a second diameter, wherein the first diameter is smaller than the second diameter and the first plunger rod flange is located below the second plunger rod flange on the shaft.

The first tubular member can be characterized into three sections: an upper portion; a lower portion; and a spring housing portion disposed between the upper portion and lower portion. The upper portion comprises a first release latch and a second release latch and a bearing seat disposed at least below the first and second release latch and aligned therewith. The first and second release latch are generally disposed on opposite sides of the upper portion and when closed, restrict vertical movement of the second tubular member in the proximal direction with respect to the first tubular member. When the first and second release latches are pushed outwardly, they are in an open configuration thereby permitting vertical movement of the second tubular member in the proximal direction with respect to the first tubular member. The bearing seat provides a surface to limit the axial movement of the second tubular member in a distal direction with respect to the first tubular member. The upper portion may further comprise a pair of grip tabs protruding outwardly from the upper portion of the first tubular member. A user's fingers can be placed underneath the grip tabs to secure the syringe device during injection.

The spring housing portion of the first tubular member comprises an annular groove sufficient to carry a spring. In certain embodiments, the spring housing portion is characterized by a first outer wall of the first tubular member and an inner wall spaced apart from the outer wall such that the space between the inner wall and outer wall provides the annular groove.

The body portion of the first tubular member provides the protective shield that covers the needle following engagement of the safety device. The internal cavity of the body portion is free of any encumbrances to prevent movement in the distal direction of the second tubular member after the safety device has been engaged such that the second tubular member may return to its original position for a subsequent injection.

The second tubular member is movable axially within the inner annular cavity of the first tubular member from an injection position to a post-injection position. The second tubular member comprises a first upper flange and a second upper flange at its proximal end and a lower flange at its distal end. The first upper flange is aligned with each of the first and second release latches such that when the first and second release latches are in a closed configuration, the first upper flange is disposed beneath the first and second release latches in a manner to prevent the second tubular member from moving axially in the proximal direction beyond the first and second release latches. The second upper flange rests on the bearing seat of the upper portion of the first tubular member thereby preventing the second tubular member from moving axially in the distal direction with respect to the first tubular member when the device is in the injection position. In certain embodiments, the second upper flange may also provide a ceiling for securing the spring in the spring housing portion while in the injection position and provides a surface by which the spring may apply force to the second tubular member directing its movement in the proximal direction in the post-injection position. The lower flange is sufficient to contact the first tubular member at a distal end of the spring housing portion when the spring is engaged thereby preventing further vertical movement in the proximal direction of the second tubular member with respect to the first tubular member. Alternatively, the first tubular member may comprise an additional flange located within the internal cavity of the body portion that engages the lower flange of the second tubular member and prevents further movement in the proximal direction of the second tubular member. At any rate, the additional flange must be positioned to permit the needle to be contained within the body portion in a post-injection position.

The syringe is disposed in the inner annular cavity of the second tubular member and is in a fixed position with respect to the second tubular member. The syringe comprises an endpiece sufficient to receive and secure a needle thereto. The syringe may be fixed to the second tubular member by any appropriate means. In one embodiment, the syringe comprises a lip at its most proximal end extending outwardly and positioned between the first upper flange and second upper flange of the second tubular member.

The plunger rod is movable axially within the syringe and comprises a proximal end and a distal end, connected by a shaft and carrying a piston to drive the fluid out of the syringe. The proximal end comprises a first plunger rod flange having a first diameter and a removable second plunger rod flange having a second diameter, wherein the first plunger rod flange is situated below the second plunger rod flange on the shaft. The first plunger rod flange extends outwardly from the plunger rod at a first distance not sufficient to engage the release latches and the second plunger rod flange extends outwardly from the plunger rod at a second distance sufficient to engage the release latches and push them outward, thereby permitting axial movement of the second tubular member in the proximal direction once pressure is removed from the second plunger rod flange.

In certain embodiments of the safety syringe device, the first plunger rod flange and the second plunger rod flange of the plunger rod each have a proximal side, and a distal side and the second plunger rod flange further comprises a peg that extends from the distal side of the second plunger rod flange and the first plunger rod flange further comprises a port located on the proximal side of the first plunger rod flange for receiving the peg. In certain embodiments, the peg that extends from the distal side of the second plunger rod flange has a circular cross section. In other embodiments, the peg that extends from the distal side of the second plunger rod flange has a non-circular cross section. In certain embodiments, of the safety syringe described herein, the peg and the port are connected by a threaded engagement.

In still other embodiments, of the safety syringe described herein, the first plunger rod flange and second plunger rod flange are connected by a string or lanyard. In yet other embodiments, the first plunger rod flange or second plunger rod flange are connected by a living hinge.

In another embodiment of the safety syringe described herein, the plunger rod further comprises a compressible spacer between the first plunger rod flange and the second plunger rod flange. In another embodiment of the safety syringe described herein, the plunger rod further comprises a collapsible or foldable spacer between the first plunger rod flange and the second plunger rod flange. In one embodiment, the spacer comprises memory foam.

The present invention further includes a method of operating the reusable safety syringe device. The method comprising the steps of: (i) simulating inserting the needle into a subject or a material; (ii) simulating injecting a fluid contained in the syringe into the subject or material by applying pressure on the first plunger rod flange to push the plunger rod in the distal direction; (iii) simulating removing the needle from the subject or the material; (iv) removing pressure from the first plunger rod flange thereby causing the spring to expand to push the second tubular member in the proximal direction thereby containing the needle in the body portion of the first tubular member; and (v) mating the second plunger rod flange to the first plunger rod flange and having the second plunger rod flange engage the first and second release latches. In specific embodiments, the method further comprises: (vi) resetting the training device by pulling the plunger rod in the proximal direction to an injection ready position. In specific embodiments, the method comprises repeating steps (i)-(vi) at least once.

DETAILED DESCRIPTION OF THE FIGURES

Figure 12:
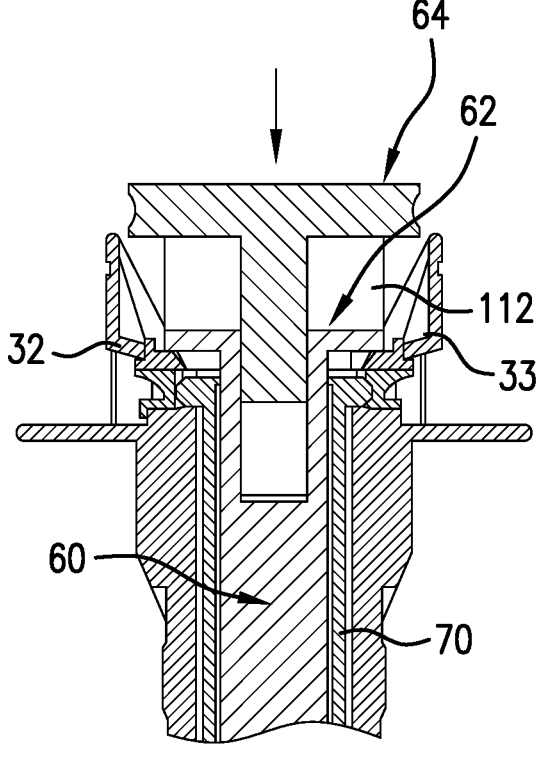

FIG. 12 shows the embodiment of the reusable safety syringe device of the present invention, wherein the plunger rod comprises a compressible spacer and wherein the first plunger rod flange and second plunger rod flange are mated to opposite faces of the compressible spacer, wherein the plunger rod is at the distal limit of its travel, wherein the distal face of the first plunger rod flange contacts the bearing seat.

Figure 13:
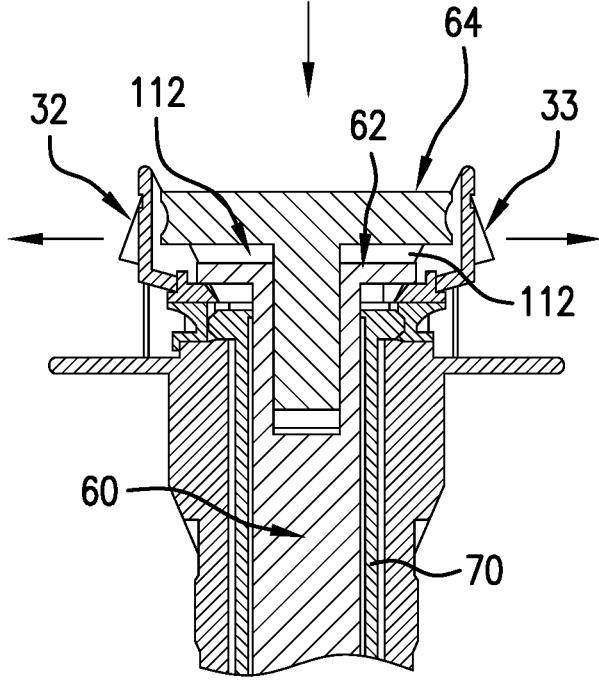

FIG. 13 shows one embodiment of the reusable safety syringe device of the present invention, wherein the plunger rod comprises a compressible spacer, wherein the first plunger rod flange and second plunger rod flange are mated to opposite faces of the compressible spacer, wherein the plunger rod is shown at the distal limit of its travel, wherein the distal face of the first plunger rod flange contacts the bearing seat, wherein the compressible spacer is fully compressed, and wherein the first plunger rod flange and second plunger rod flange are in close proximity to each other and the second plunger rod flange has engaged the release latches.

Figure 14:
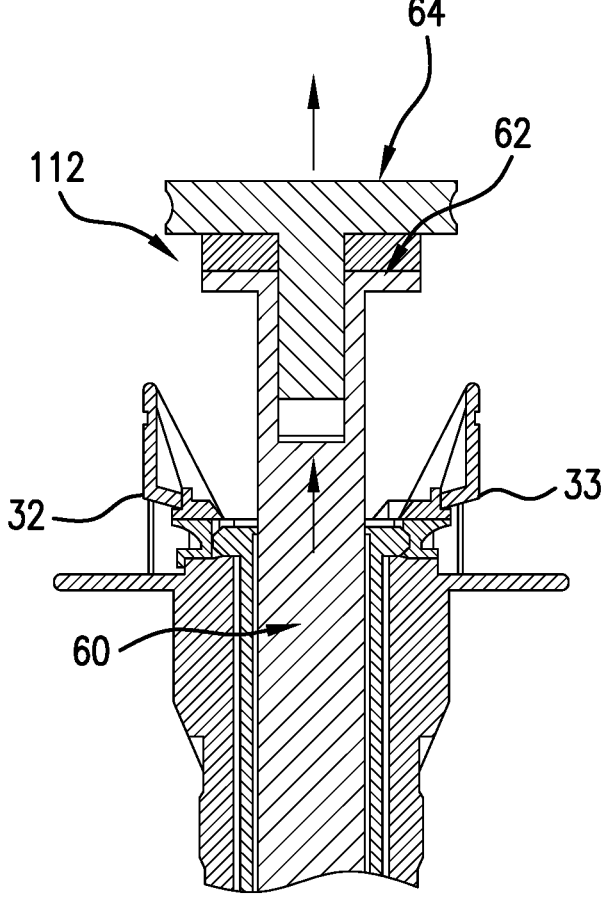

FIG. 14 shows one embodiment of the reusable safety syringe device of the present invention wherein the plunger rod includes a compressible spacer, and wherein the release latches have returned to their original positions, wherein the release latches have released the first plunger rod flange, wherein the plunger rod is moving in the proximal direction, and wherein the compressible spacer is re-expanding.

DETAILED DESCRIPTION OF THE INVENTION

Definitions

For the purposes of clarity and consistency, the term "proximal" refers to a direction away from the body of the patient and towards the device. The term "distal" refers to a direction towards the body of the patient and away from the device.

Figure 1A:
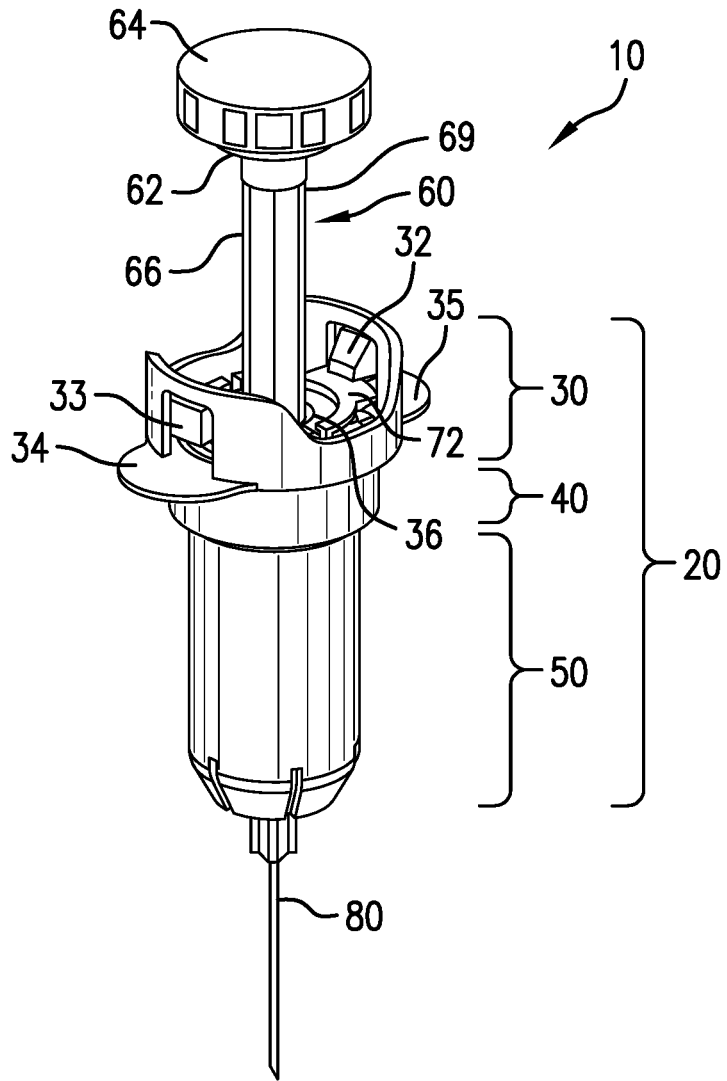
FIG. 1A shows one embodiment of the reusable safety syringe device of the present invention.
Figure 1B:
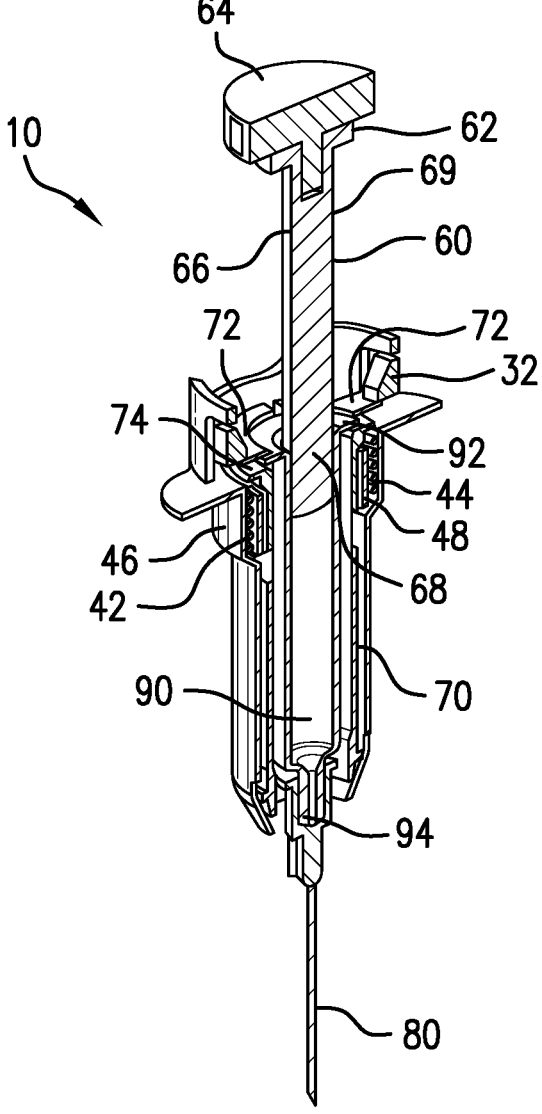
FIG. 1B is a cross section of the reusable safety syringe device depicted in FIG. 1A.
Figure 2A:
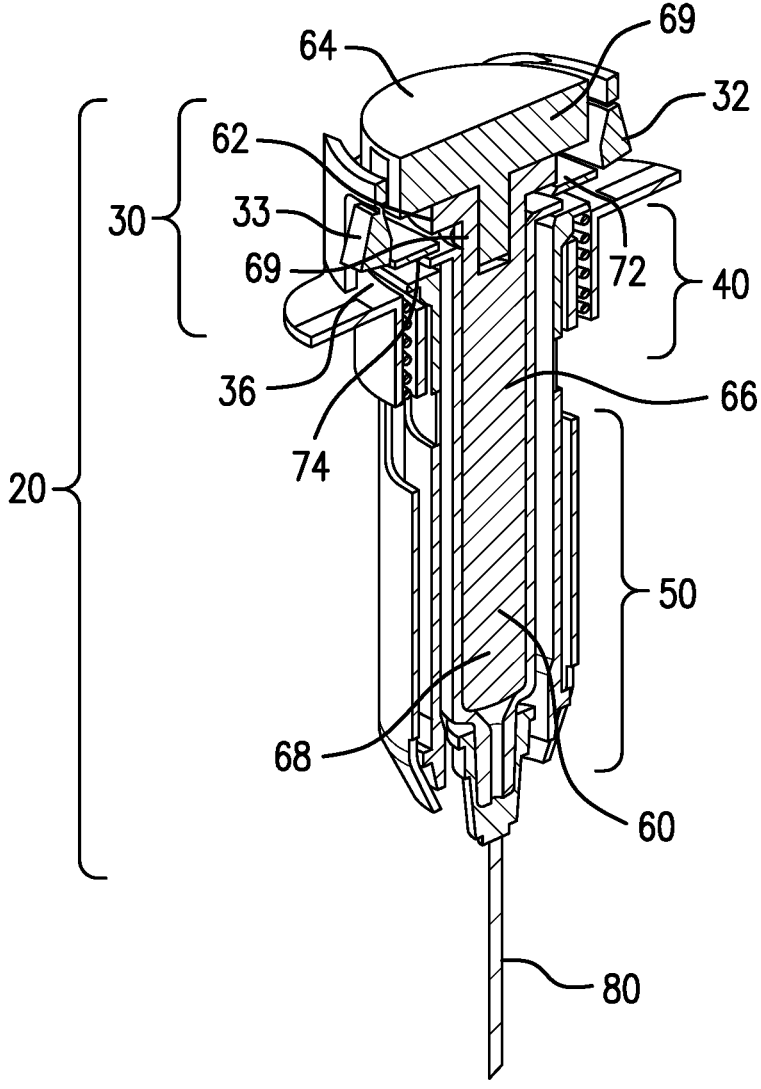
FIG. 2A is a cross section of an embodiment of the reusable safety syringe device during the injection.

Described herein is a plunger rod design used in conjunction with a reusable safety syringe device. One embodiment of the reusable safety syringe device of the present invention is depicted in FIGS. 1A, 1B, 2A, and 2B. The device 10 comprises a standard syringe 90 for injecting a liquid. Syringe 90 has an open proximal end provided with a lip 92 and a distal end providing an end piece 94 sufficient to secure needle 80, an optional syringe closure plug (not shown) or an optional needle carrier (not shown). The syringe 90 includes a plunger rod 60 moveable axially therein between a pre-injection position as shown in FIGS. 1A and 1B and a post-injection position as shown in FIG. 2A. Plunger rod 60 has a proximal end 69 comprising a first plunger rod flange 62 and a second plunger rod flange 64, and a distal end 68, connected by a shaft 66. The first plunger rod flange 62 is positioned distal to the second plunger rod flange 64, which is removable, on the shaft 66. The first plunger rod flange 62 has a first diameter and the second plunger rod flange 64 has a second diameter, wherein the first diameter is smaller than the second diameter.

The device 10 further comprises safety components referred to herein as first tubular member 20 and second tubular member 70 housed inside first tubular member 20 and substantially coaxial therewith. The first tubular member 20 and the second tubular member 70 are movable axially relative to each other between a first position, referred to as a locked position of the needle, as shown in FIGS. 1A, 1B and 2A, and a second position, referred to as an engaged position of the needle, as shown in FIG. 2B.

First tubular member 20 comprises upper portion 30, spring housing portion 40, and body portion 50. It should be understood that these portions are defined herein for purposes of orientation of various aspects of the device and is not intended to require the device to possess distinct and visually separable portions. Upper portion 30 comprises release latches 32, 33 positioned diametrically opposite. Release latches 32, 33 are elastically deformable in a radial direction. Release latches 32, 33 are depicted in FIGS. 1A and 1B in a locked configuration such that they protrude inwardly and prevent movement in the proximal direction of second tubular member 70 at first upper flange 72 and in an open configuration as shown in FIG. 2A where second plunger rod flange 64 engages release latches 32, 33 causing them to protrude outwardly. Upper portion 30 may further comprise grip tabs 34, 35 designed to be gripped by the fingers of a user to simulate the injection of a liquid by axially moving plunger rod 60 towards grip tabs 34, 35.

Spring housing portion 40 may be constructed in a number of different manners. In one embodiment, spring housing portion 40 is formed by outer wall 46 and inner wall 48 where spring 42 is housed in groove 44 between outer wall 46 and inner wall 48. Groove 44 serves to position spring 42 both axially and radially. Spring 42 bears against second upper flange 74 formed on second tubular member 70, and on an inner seat (not shown) projecting inwardly from first tubular member 20 and positioned at the bottom of groove 44 housing spring 42. In other embodiments, inner wall 48 may not be necessary so long as the second tubular member 70 is sufficient to contain spring 42 between it and outer wall 46.

Figure 2B:
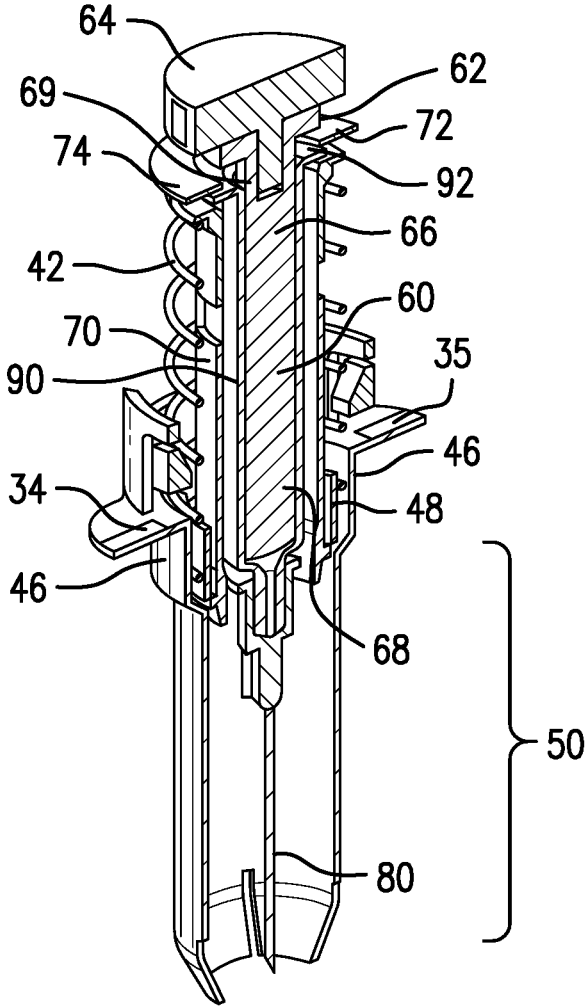
FIG. 2B is a cross section of an embodiment of the reusable safety syringe device following injection with the safety shield engaged.

Body portion 50 provides the protective sheath when device 10 is in the engaged position as shown in FIG. 2B thereby encompassing needle 80.

Syringe 90 is housed in second tubular member 70. More particularly, syringe 90 is prevented from moving axially in second tubular member 70 by lip 92 positioned between first upper flange 72 and second upper flange 74 of second tubular member 70. Where appropriate, the radial and transverse clearances between lip 92 and the housing formed by first and second upper flanges 72 and 74 can be limited by cooperation between complementary shapes.

Second upper flange 74 also serves to prevent axial movement in the distal direction of second tubular member 70 with respect to first tubular member 20 by engaging bearing seat 36 on upper portion 30 as shown in FIGS. 2A and 2B.

Figure 3:
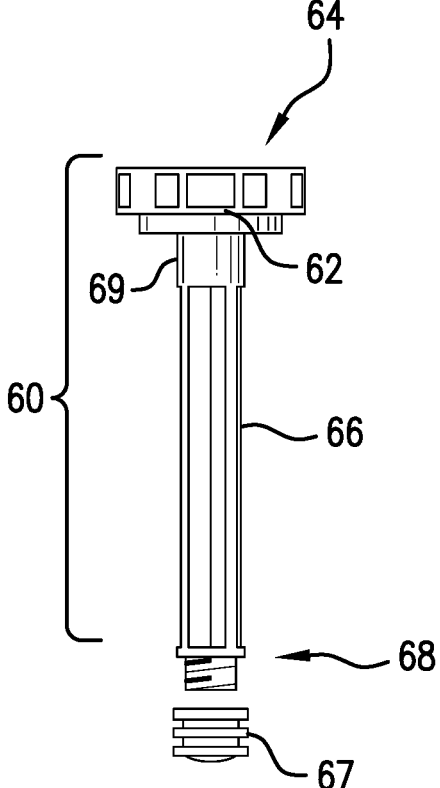
FIG. 3 shows an embodiment of a plunger rod and plunger used in a reusable safety syringe device of the present invention.
Figure 4:
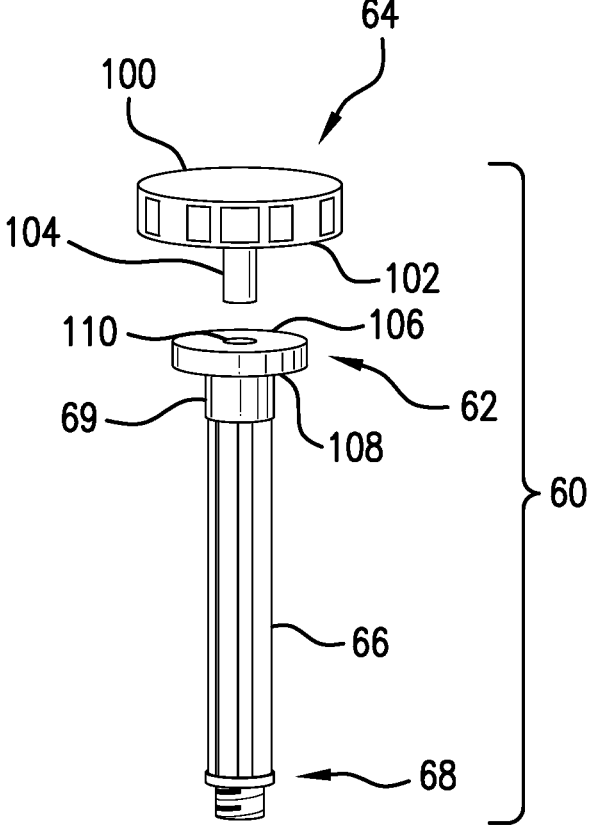
FIG. 4 shows an embodiment of a plunger rod used in a reusable safety syringe device of the present invention.

FIG. 3 shows an embodiment of a plunger rod of the present invention, used in a safety syringe described herein. Plunger rod 60 has a proximal end 69 comprising a first plunger rod flange 62 and a second plunger rod flange 64, and a distal end 68, connected by a shaft 66. A plunger 67 is typically attached to the distal end 68 of plunger rod 60. As shown in FIG. 3, the first plunger rod flange 62 has a first diameter and the second plunger rod flange 64 has a second diameter, wherein the first diameter is smaller than the second diameter. In certain embodiments, the second plunger rod flange is removable from the first plunger rod flange. As shown in FIG. 4, plunger rod 60 has a proximal end 69 comprising a first plunger rod flange 62 and a second plunger rod flange 64, and a distal end 68, connected by a shaft 66 and second plunger rod flange 64 is removable from first plunger rod flange 62. As shown in FIG. 4 second plunger rod flange 64 has a proximal side 100 and a distal side 102, wherein the second plunger rod flange 64 comprises a peg 104 that extends from the distal side 102 of the second plunger rod flange 64. To accommodate peg 104, the first plunger rod flange 62 has a proximal side 106 and a distal side 108 and wherein the first plunger rod flange comprises a port 110 located on the proximal side 106 of the first plunger rod flange 62 for receiving the peg 104.

As shown in FIG. 4, the first plunger flange and the second plunger flange are separate and not connected. In other embodiments, the first plunger flange and second plunger flange are connected. In certain embodiments, the first plunger flange and the second plunger flange are connected by a string. In certain embodiments, the first plunger flange and the second plunger flange are connected by a lanyard. In certain embodiments, the first plunger flange and the second plunger flange are connected by a living hinge.

Figure 5:
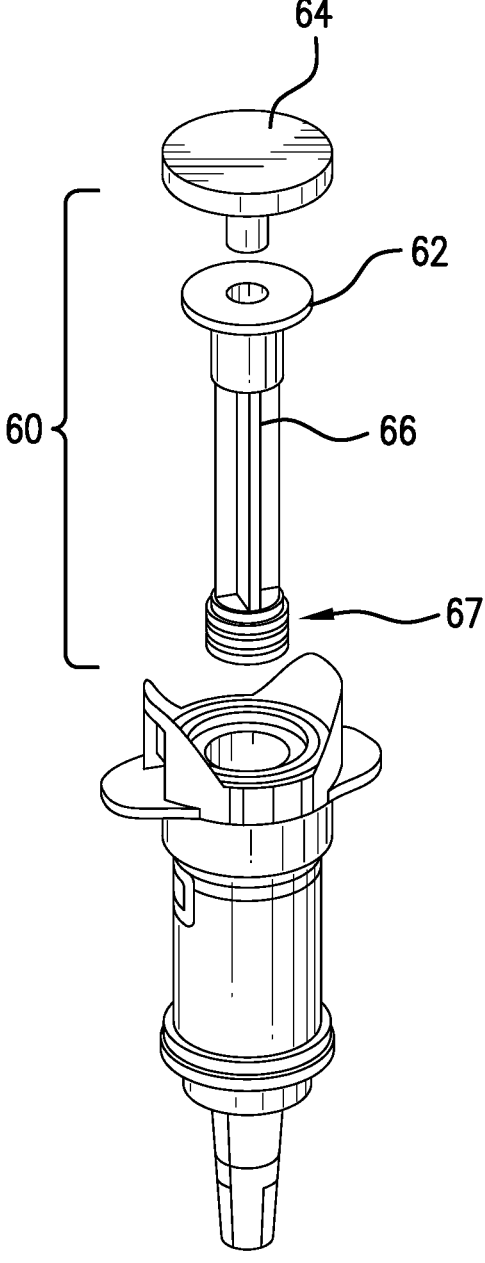
FIG. 5 shows one embodiment of the reusable safety syringe device of the present invention, wherein the second plunger rod flange of the plunger rod is separated from the first plunger rod flange of the plunger rod.

FIG. 5 shows the plunger rod 60 and a plunger 67 having a first plunger rod flange 62 and a second plunger rod flange 64 connected by a shaft 66. Depicted in FIG. 5, the plunger rod 60 is being placed in the first tubular member 20 which houses the syringe and second tubular member.

Figure 6:
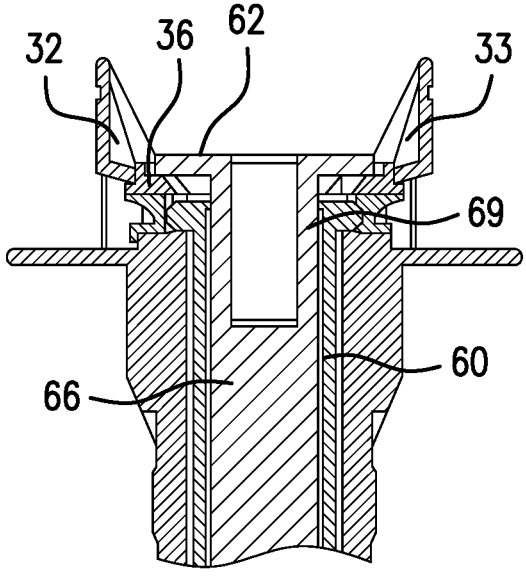
FIG. 6 shows one embodiment of the reusable safety syringe device of the present invention, wherein the first plunger rod flange of the plunger rod is contacting the bearing seat activating the safety device and covering the needle.
Figure 7:
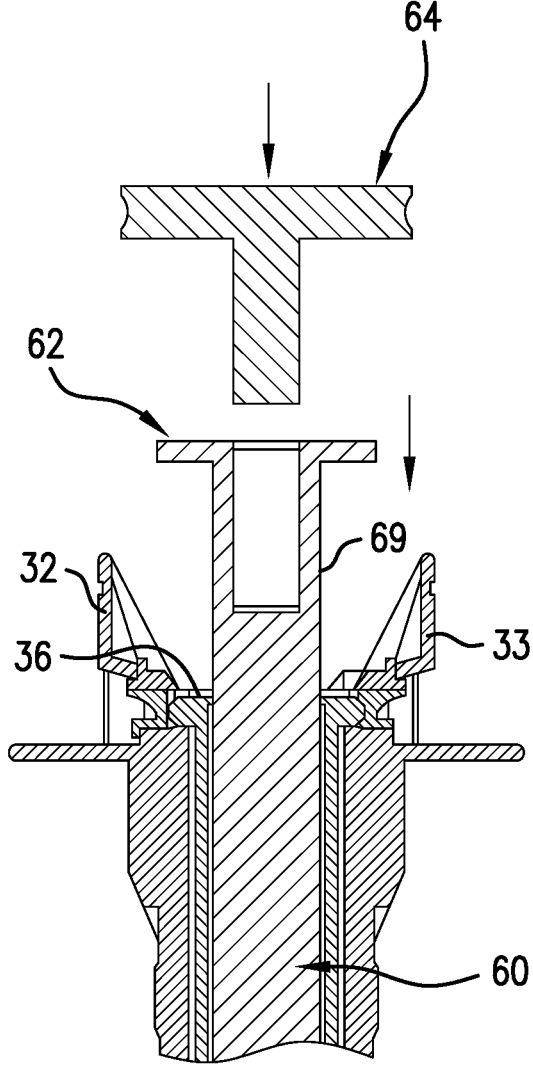
FIG. 7 shows one embodiment of the reusable safety syringe device of the present invention, wherein the second plunger rod flange is being mated with the first plunger rod flange.
Figure 8:
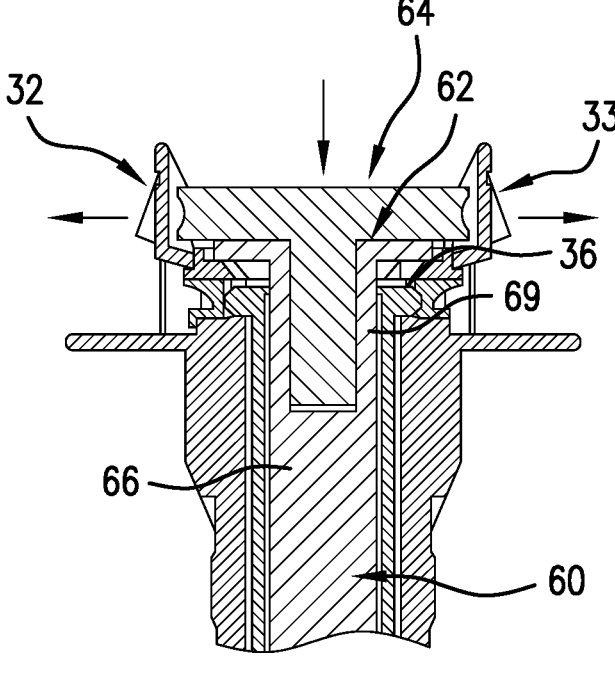
FIG. 8 shows one embodiment of the reusable safety syringe device of the present invention, wherein the first plunger rod flange and second plunger rod flange are mated, and the second plunger rod flange has engaged the release latches.
Figure 9:
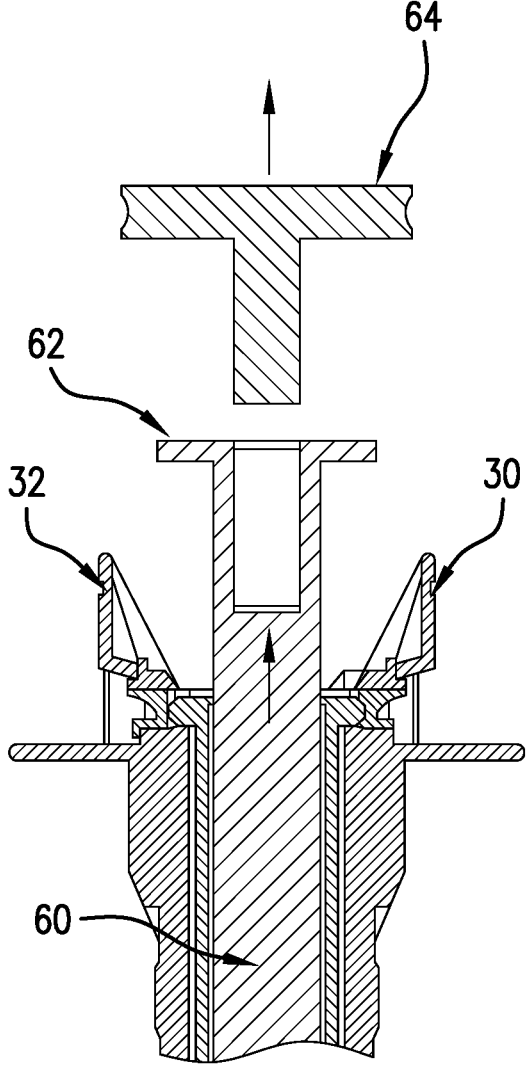
FIG. 9 shows one embodiment of the reusable safety syringe device of the present invention, wherein the second plunger rod flange is being removed from the first plunger rod flange.

When the ejection stroke is complete, the first plunger rod flange 62 contacts bearing seat 36, limiting further travel of plunger rod 60. The diameter of first plunger rod flange 62 is sufficiently small that it does not contact release latches 32, 33 whereby the second tubular member is prevented from retracting in the proximal direction, as shown in FIG. 6. This position simulates the injection state of the device. To enable retraction of the second tubular member, a second plunger rod flange 64 is removably attached to the proximal end 69 of plunger rod 60, wherein first plunger rod flange 62 and second plunger rod flange 64 are mated together so that they are in contact with each other and radially aligned, as shown in FIG. 7 and FIG. 8. The diameter of second plunger rod flange 64 is sufficiently large that applying second plunger rod flange 64 to first plunger rod flange 62 causes the outer edge of second plunger rod flange 62 to contact release latches 32, 33 and displace them radially, as shown in FIG. 8, whereby they release first upper flange and whereby the second tubular member is free to travel axially in the proximal direction, as shown in FIG. 9. In this position, the device is ready to be reused to simulate another injection sequence.

Figure 10:
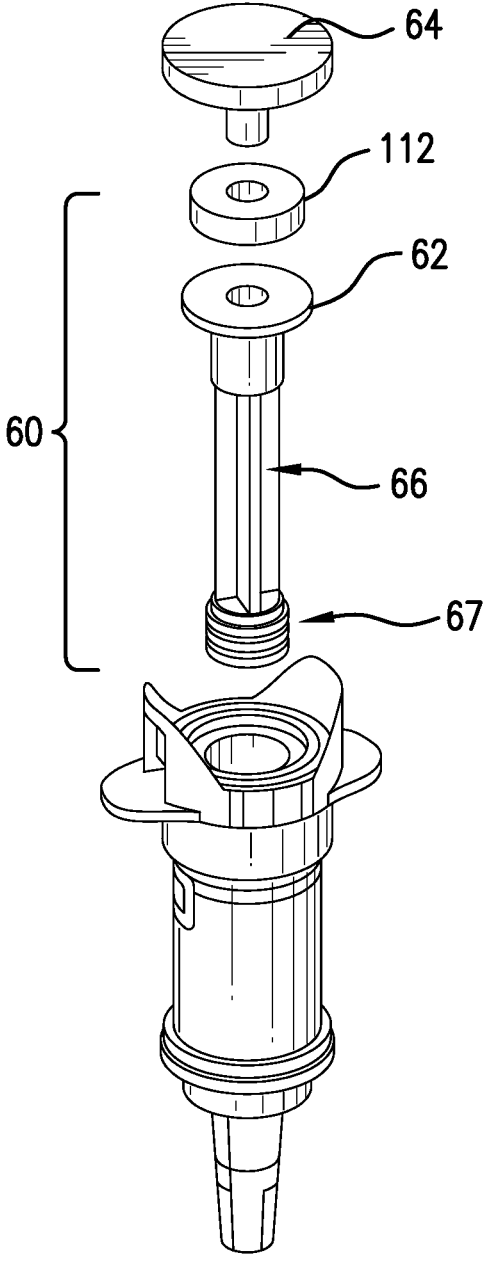
FIG. 10 shows the embodiment of the reusable safety syringe device of the present invention, wherein the plunger rod includes a compressible spacer, and wherein the plunger rod, first plunger rod flange, spacer, and second plunger rod flange are shown in an exploded view.
Figure 11:
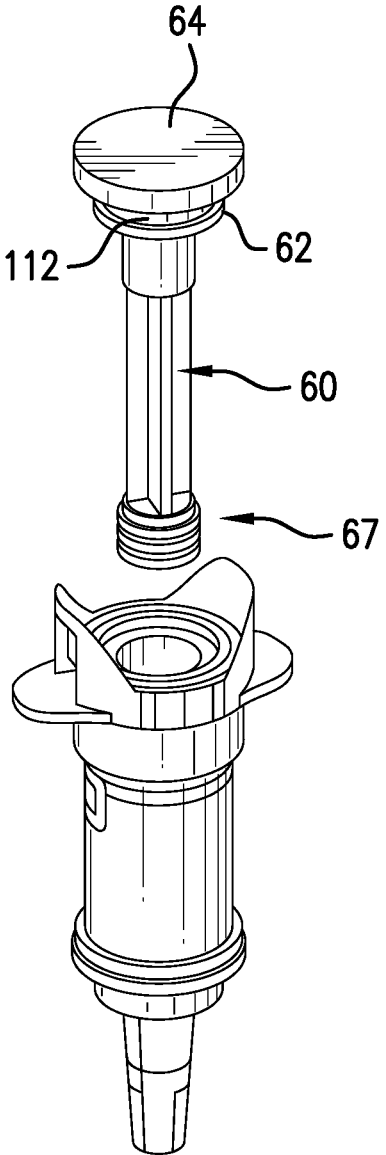
FIG. 11 shows another embodiment of the reusable safety syringe device of the present invention shown in FIG. 10, and wherein the plunger rod comprises a first plunger rod flange and a second plunger rod flange mated to a compressible spacer.

In certain embodiments of the safety syringe described herein, the plunger rod and plunger 67 further comprises a compressible spacer between the first plunger rod flange and the second plunger rod flange. In an alternate embodiment, the plunger rod further comprises a collapsible or foldable spacer between the first plunger rod flange and the second plunger rod flange. In one embodiment, a layer of visco-elastic foam 112, also known as memory foam, is situated between first plunger rod flange 62 and second plunger rod flange 64, as shown in FIG. 10 and FIG. 11. The diameter of first plunger rod flange 62 is sufficiently small that it does not contact release latches 32, 33, whereby the second tubular member is prevented from retracting in the proximal direction. On initial contact between the first plunger rod flange 62 and the second tubular member, the second plunger rod flange 64 is prevented from contacting release latches 32 and 33 by the foam 112, as shown in FIG. 12. With continued applied pressure, foam 112 compresses sufficiently to allow the second plunger rod flange 64 to come into very close proximity to first plunger rod flange 62. Second plunger rod flange 64 has a sufficiently large diameter to displace release latches 32, 33 radially outward, as shown in FIG. 12 and FIG. 13. In this position, second plunger rod flange 64 displaces release latches 32,33 sufficiently to cause them to release first plunger rod flange 62, as shown in FIG. 14, whereby the second tubular member 70 is free to travel axially in the proximal direction and foam 112 begins to slowly re-expand.

Suitable compressible spacer properties can include, but are not limited to, sufficiently slow recovery to cause the compressible spacer to remain compressed for a sufficient time until the second tubular member is released and is free to retract in the proximal direction, and the ability to be ready to be reused to simulate another injection sequence. The recovery time of the compressible spacer preferably can be minimum of at least 0.5 seconds and a maximum of 5 minutes, but can extend beyond this range so long as the reusable safety syringe remains operable. Furthermore, the stiffness of the foam can comprise a range that would prevent full compression unless the applied compressive force were a minimum value. Such a minimum stiffness value would depend on a variety of factors including the size of the syringe. However, a typical minimum stiffness value would be a 5 lb. ILD value. The ILD value is the force required to compress a 15 inches wide by 15 inches long by 4 inches thick foam sample by 25% of its original thickness under standard test conditions. The compressible spacer may comprise a wide range of other properties, but in general a minimum density of 6 lb./cu. ft is preferred.

In select embodiments, the needle is made of a plastic fiber or alternative flexible material (e.g., a monofilament) intended not to pinch or harm a subject employing the device. The simulated injection may be carried out on a subject or alternative injection material. The term "subject" as used herein refers to a mammal, and in particular a human. The injection material can be any material suitable for injection material as recognized by one of skill in the art, including for instance an injection pad. The needle may be tubular in cross section wherein it can transport fluid from the glass syringe vial to a practice target. In an alternate embodiment, needle is tubular but with a restricted diameter whereby dispensing air from the syringe provides a similar resistance to motion as that encountered when dispensing a liquid.

In an alternate embodiment, needle comprises a solid cross section, but venting of air from the syringe is provided by small ports create in the distal end of the syringe barrel. In an alternate embodiment, reduced flow restriction may be created when retracting the plunger rod in the proximal direction by a check valve in the stopper or in the syringe barrel.

The plunger rod is movable axially within the syringe and comprising a proximal end and a distal end carrying a piston to drive the fluid out of the syringe. The proximal end comprises a user contact surface and a release flange disposed distally from the user contact surface.

The invention is not limited to the embodiments described above. One of ordinary skill in the art could appreciate modifications to the embodiment described above that will perform the same reusable function.

What is claimed:

1. A plunger rod for use with a safety syringe comprising a proximal end and a distal end, wherein the proximal end and distal end are connected by a shaft, wherein the proximal end comprises a first plunger rod flange having a first diameter and a second plunger rod flange having a second diameter, and wherein the first diameter is smaller than the second diameter and the first plunger rod flange is positioned distal to the second plunger rod flange, wherein the first plunger rod flange and second plunger rod flange are connected by a living hinge, string or lanyard.

2. The plunger rod of claim 1, wherein the second plunger rod flange is removable from the first plunger rod flange.

3. The plunger rod of claim 1, wherein the second plunger rod flange has a proximal side and a distal side, wherein the second plunger rod flange comprises a peg that extends from the distal side, wherein the first plunger rod flange has a proximal side and a distal side and wherein the first plunger rod flange comprises a port located on the proximal side of the first plunger rod flange for receiving the peg.

4. The plunger rod of claim 3, wherein the peg that extends from the distal side of the second plunger rod flange has a circular cross section.

5. The plunger rod of claim 3, wherein the peg that extends from the distal side of the second plunger rod flange has a non-circular cross section.

6. The plunger rod of claim 3, wherein the peg and the port are connected by a threaded engagement.

7. The plunger rod of claim 3, wherein the plunger rod further comprises a compressible spacer between the first plunger rod flange and the second plunger rod flange.

8. The plunger rod of claim 3, wherein the spacer comprises memory foam.

9. The plunger rod of claim 3, wherein the spacer is a collapsible or foldable spacer.

* * * * *